(12) United States Patent
Mueller

(10) Patent No.: US 6,845,650 B2
(45) Date of Patent: Jan. 25, 2005

(54) GAS CHROMATOGRAPH

(75) Inventor: Friedhelm Mueller, Linkenheim-Hochstetten (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/600,351

(22) Filed: Jun. 23, 2003

(65) Prior Publication Data

US 2004/0083788 A1 May 6, 2004

Related U.S. Application Data

(63) Continuation of application No. PCT/DE01/04819, filed on Dec. 20, 2001.

(30) Foreign Application Priority Data

Dec. 21, 2000 (DE) .................................... 100 64 138

(51) Int. Cl.[7] .............................................. G01N 30/02
(52) U.S. Cl. ....................................... 73/23.4; 73/23.36
(58) Field of Search .............................. 73/23.4, 23.39, 73/23.41, 23.22, 23.35, 23.36

(56) References Cited

U.S. PATENT DOCUMENTS

| | | | | |
|---|---|---|---|---|
| 3,141,323 A | * | 7/1964 | Taylor et al. ............... | 73/23.35 |
| 3,159,019 A | * | 12/1964 | De Ford ..................... | 73/23.26 |
| 3,263,488 A | * | 8/1966 | Martin ........................ | 73/23.39 |
| 3,304,159 A | * | 2/1967 | Hinsvark ..................... | 436/115 |
| 3,330,150 A | * | 7/1967 | Lloyd et al. ................ | 73/23.39 |
| 3,403,978 A | * | 10/1968 | Favre .......................... | 436/158 |
| 3,451,779 A | * | 6/1969 | Hozumi ....................... | 422/96 |
| 3,483,731 A | * | 12/1969 | Sanford et al. ............ | 73/23.35 |
| 3,937,061 A | * | 2/1976 | Rhodes, Jr. .................. | 73/23.4 |
| 4,181,006 A | * | 1/1980 | DeFord ....................... | 73/23.36 |
| 4,546,649 A | * | 10/1985 | Kantor ........................ | 73/168 |
| 4,935,145 A | | 6/1990 | Cortes et al. | |
| 4,952,126 A | | 8/1990 | Hanaoka et al. | |
| 5,240,604 A | * | 8/1993 | Cortes et al. ............. | 210/198.2 |

FOREIGN PATENT DOCUMENTS

| | | |
|---|---|---|
| EP | 0 406 757 A2 | 1/1991 |
| JP | 59-75151 A | 4/1984 |
| JP | 61-212759 A | 9/1986 |
| JP | 03-3310 A | 1/1991 |
| JP | 9-292383 A | 11/1997 |

* cited by examiner

*Primary Examiner*—Michael Cygan
(74) *Attorney, Agent, or Firm*—Sughrue Mion, PLLC

(57) ABSTRACT

A gas chromatograph in which the substances of a substance mixture that is to be analyzed are separated in a separation device and are detected in a detector device. An evaluation device (10) provides a result (11) in the form of a quantitative determination of given substances depending on the detector signals. To obtain a relatively rapid analysis result, an additional detector device (13), which generates additional detector signals (16) based on the substances that at this stage have not been completely separated, is located in the path of the separation device (6). A computational unit (18) provides a quantitative determination of at least one part of the given substances as a further result (20), based on the additional detector signals (16). This somewhat imprecise but rapid result can be used for rapid control or regulatory interventions in a process (4). The computational precision of the computational unit (18) can be adaptively improved, based on the result of the evaluation device (10) which is more precise but takes longer to obtain.

9 Claims, 2 Drawing Sheets

5 Dosing Unit
10 Evaluation Device
12 Process Control Device
18 Computational Unit
19 Computational Algorithm
21 Memory Unit
22 Comparator Unit
24 Correction Algorithm

- 5 Dosing Unit
- 10 Evaluation Device
- 12 Process Control Device
- 18 Computational Unit
- 19 Computational Algorithm
- 21 Memory Unit
- 22 Comparator Unit
- 24 Correction Algorithm 32 Detector Circuit

GAS CHROMATOGRAPH

This is a Continuation of International Application PCT/DE01/04819, with an international filing date of Dec. 20, 2001, which was published under PCT Article 21(2) in German, and the disclosure of which is incorporated into this application by reference.

FIELD OF AND BACKGROUND OF THE INVENTION

The invention relates to a gas chromatograph with a separation device, which separates the substances of a substance mixture that is supplied to it in a dosed manner and flows through it. The gas chromatograph also has a detector device, which is arranged downstream of the separation device and which generates detector signals as a function of the arriving separated substances, and an evaluation device, which is connected to the detector device and which provides a quantitative determination of specified substances as the result, based on the detector signals.

A drawback of chromatography, particularly of process chromatography, is the time required to separate the substances in the substance mixture to be analyzed. This separation time can be shortened by using high-performance separation columns or by predefined temperature patterns during the separation, but the rates of analysis afforded by quasi-continuous processes, such as spectrometry, cannot be reached. However, in open or closed-loop process control, rapid process changes must be rapidly detected to be able to correct them.

OBJECTS OF THE INVENTION

Thus, one object of the invention is to provide a gas chromatograph that can provide relatively fast analysis results.

SUMMARY OF THE INVENTION

According to one formulation of the invention, this and other objects are attained in a gas chromatograph, e.g. of the initially described type, by arranging an additional detector device in the path of the separation device. This additional detector device produces additional detector signals as a function of the substances that at this stage have not been completely separated. A computational unit connected to the additional detector device provides a quantitative determination of at least a portion of the specified substances as a further result, based on the additional detector signals.

The additional result provided by the computational unit, which is based on an incomplete separation of the substances, is less precise than the result provided by the evaluation device after the substances have been completely separated. However, it is available substantially earlier. Despite the incomplete separation of the substances in the region where the additional detector device is arranged, the individual substances can already be quantitatively determined, subject to a certain inaccuracy. This is true because in chromatography, the substances to be analyzed and thus the additional detector signals to be expected from the additional detector device (position and shape of the peaks) are known per se. In each case, substantial changes in the respective proportions of the individual substances can be detected early in the mixture of substances being analyzed.

The evaluation device and the computational unit can thus advantageously be used to control a process control device, e.g., an open and/or closed loop process control device. If the rates of change of the additional result of the computational unit are relatively high, this process control device uses the additional result at least predominantly, and otherwise uses the other result of the evaluation unit, for the open and/or closed loop control. As long as the process to be controlled is stable, the changes occurring in the composition of the mixture of substances to be analyzed are small and slow. In this case, the process control device uses the precise results provided by the evaluation device after complete separation of the substances in order to make precision corrections in the process flow, for optimizing the process result, e.g., with respect to quality or yield.

If, on the other hand, the process is unstable, i.e., if the composition of the mixture of substances changes rapidly and significantly, the process control device must intervene in the process to regulate and/or control it as quickly as possible. In this case, the speed of the intervention in the process is more important than its accuracy. For this reason, the additional results, which are less accurate but faster, are used for these rapid control interventions in the process.

To further increase the accuracy of the additional results provided by the computational unit, the computational unit preferably includes a computational algorithm with variable parameters for the quantitative determination of the predefined substances or a part thereof. A memory unit is available for storing the additional result provided by the computational unit. A comparator unit is available for comparing the result of the evaluation device with the stored additional result of the computational unit. The computational unit includes a correction algorithm that changes the parameters of the computational algorithm as a function of the variance between the result of the evaluation device and the stored additional result of the computational unit, in particular so as to reduce this variance. In this manner, the computational algorithm is continuously optimized, so that, in accordance with the application or the learning capacity of the computational algorithm, the additional result provided in advance by the computational unit can have a very high accuracy. Optimizing the computational algorithm is comparatively simple insofar as the mixtures of substances to be analyzed and thus the detector signals to be expected of the additional detector device are known per se, as mentioned above.

For the additional detector device, only such detectors that do not destroy the substance mixture come into consideration. These include, for instance, a thermal conductivity detector, a suitable optical detector or a detector using acoustic surface waves. To avoid impairing the separation efficiency of the separation device, the measuring path of the additional detector device through which the substance mixture flows is preferably configured in such a way that its cross-sectional dimensions correspond at least approximately to the cross-sectional dimensions of the separation device. This prevents interference with the dosing plug, which is preferably used for introducing the substance mixture into the separation device and which should be as short and sharply defined as possible, at the location of the additional detector device.

Based on a preferred embodiment of the chromatograph according to the invention, the additional detector device is a thermal conductivity detector with heating resistors arranged in a bridge circuit. Two of these heating resistors are disposed in the measuring path in the two different halves of the bridge, diagonally opposite each other. The other two heating resistors lie in a reference path. The thermal conductivity detector can function alternately as the detector device and as the additional detector device. The two other heating resistors are then disposed in a measuring path of the detector device arranged downstream of the separation device through which the substance mixture flows. The measuring path of each of the two detector devices is, at the same time, the reference path of the respectively other detector device. The dosing plug of the substance mixture to be analyzed first passes through the additional detector device and only subsequently reaches the detector device, i.e., it never flows through the two detector devices simultaneously. As a result, one of the two measuring paths of the detector device and the additional detector device through which the substance mixture does not flow at any given moment can always be used as a reference path.

BRIEF DESCRIPTION OF THE DRAWINGS

The invention will now be described in greater detail with reference to the drawing figures in which.

DETAILED DESCRIPTION OF THE PREFERRED EMBODIMENTS

Figure 1:
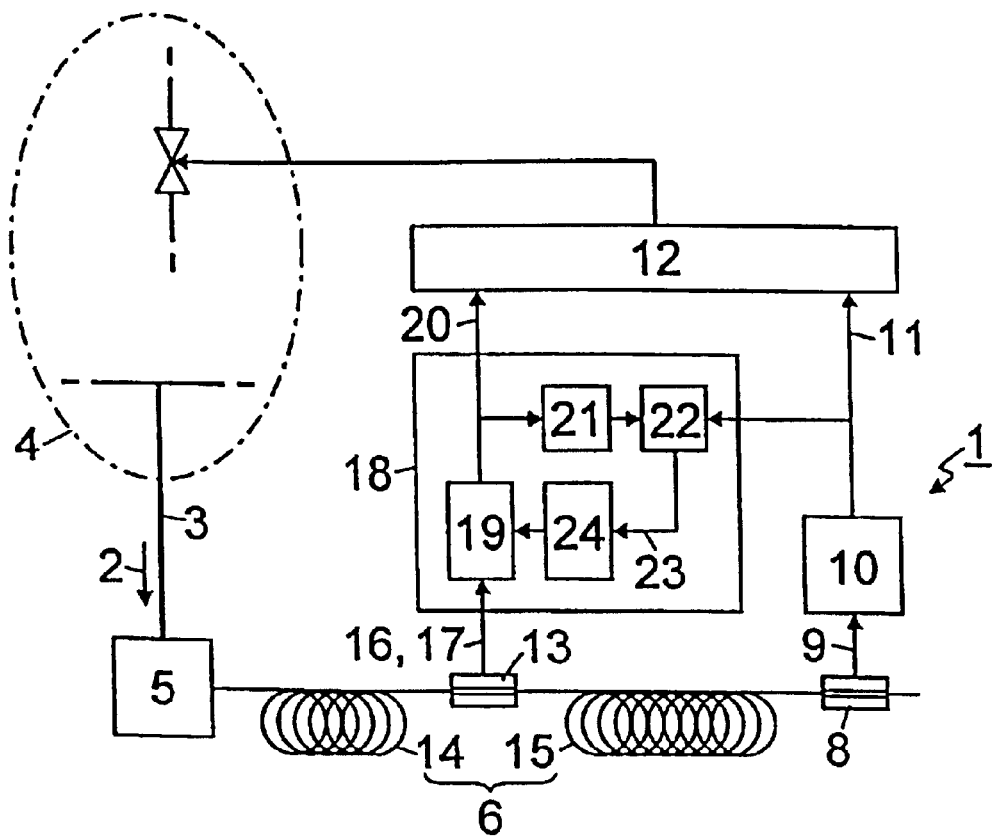
FIG. 1 is an exemplary embodiment of the gas chromatograph according to the invention.
Figure 2:
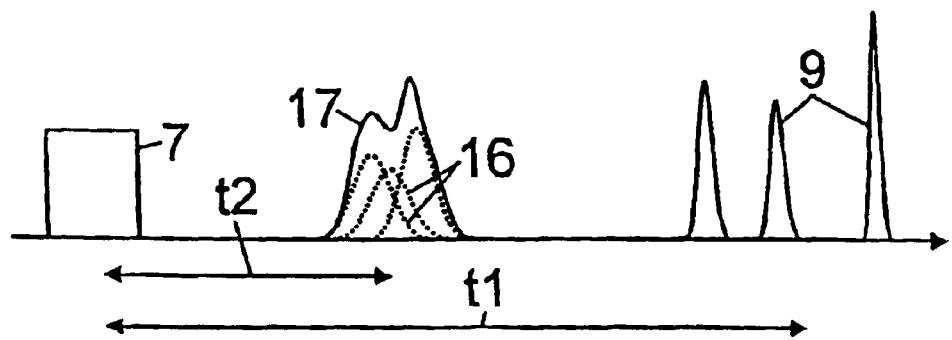
FIG. 2 is an example of the detector signals and the additional detector signals provided by the detector device and the additional detector device and FIG. 3 is an exemplary embodiment of the detector device and the additional detector device.

FIG. 1 shows a chromatograph 1, in particular a gas chromatograph, for analyzing a substance mixture 2, which is removed from a technical process 4 via a pipe 3. For this purpose, the substance mixture 2 is processed, e.g., evaporated, for chromatographic analysis in a processing and dosing unit 5, and is fed in dosed form to a separation device 6. Dosing occurs in such a way that a dosing plug 7, which is as short and as sharply defined as possible, is extracted from the substance mixture, as illustrated in FIG. 2. The separation device 6 is configured to separate the substances contained in the dosed substance mixture 2 as the mixture flows through the separation device 6, so that the individual substances successively reach a detector device 8 disposed at the end of the separation device 6, where they are detected. In the exemplary embodiment shown, the detector device 8 is preferably a thermal conductivity detector.

For each detected substance, this thermal conductivity detector generates a typical detector signal 9 in the form of a peak, as illustrated in FIG. 2. The height and area of the peak depend on the amount and the thermal conductivity of the detected substance. An evaluation device 10 disposed downstream of the detector device 8 quantitatively determines selected substances of the substance mixture 2 being analyzed, based on the detector signals 9. The result 11 thus obtained, i.e., the quantities or concentrations of the selected substances, is supplied to an open and/or closed loop process control device 12, which intervenes in the process 4, by controlling or regulating it, as a function of the result 11.

Due to the separation time t1 required to completely separate the substances of the substance mixture 2 to be analyzed (FIG. 2), the results 11 are available with a substantial delay after the substance mixture 2 has been removed from the process 4. As a consequence, they are essentially suitable only for long-term open or closed-loop process control, e.g., to make precision corrections in a stable process 4, for example to optimize the quality or yield of products produced in the process 4. If the process 4 is unstable, however, rapid interventions in the process 4 are usually required to counteract the unstable process flow. In this case the speed with which the intervention occurs is usually more important than its accuracy. To enable such rapid process interventions, an additional detector device 13 is arranged in the path of the separation device 6, which separates the substances of the substance mixture 2 only incompletely but detects them in a relatively short time t2 (FIG. 2) after the substance mixture 2 has been removed from the process 4. As will be explained in greater detail below, the detector device 13 is configured and arranged in such a way that it does not affect the separation efficiency of the separation device 6. In the exemplary embodiment shown, the separation device 6 has two separation column sections 14 and 15 between which the additional detector device 13 is inserted "inline." The measuring path of the additional detector device 13 through which the substance mixture 2 flows has at least approximately the same cross-sectional interior dimensions as the separation column sections 14 and 15.

As FIG. 2 shows, the detector signals 16 (peaks) supplied by the additional detector device 13 overlap into a sum signal 17 because of the incomplete separation of the substances. However, because the substances contained in the substance mixture 2 being analyzed, and thus the peak shapes of the individual detector signals 16 to be expected, are known, the individual substances can be at least roughly quantitatively determined using the sum signal 17. This is accomplished in a computational unit 18 using a computational algorithm 19. The additional result 20 thus obtained is provided to the open and/or closed-loop process control device 12. As long as the process 4 is stable, the composition of the substance mixture 2 does not change or changes only slowly and to a minor extent. On the other hand, rapid significant changes in the substance mixture indicate an unstable process flow. Such rapid changes in the composition of the substance mixture 2 are detected with sufficient accuracy by the additional detector device 13 and the downstream computational algorithm 19. To correct an unstable process flow rapidly, the open and/or closed loop process control device 12 uses the additional result 20 supplied by the computational unit 18 exclusively or at least predominantly.

To optimize the computational algorithm 19 continuously, the additional result 20 supplied by this algorithm is intermediately stored in a memory unit 21 until the result 11 provided by the evaluation device 10 is available. The two results 11 and 20 are compared in a comparator unit 22. Any variances 23 between the two results 11 and 20 are provided to a correction algorithm 24, which changes the parameters of the computational algorithm 19 to achieve a reduction of this variance 23, i.e., the computational error. An example of a suitable correction algorithm 24 is the so-called descending gradient method.

Figure 3:
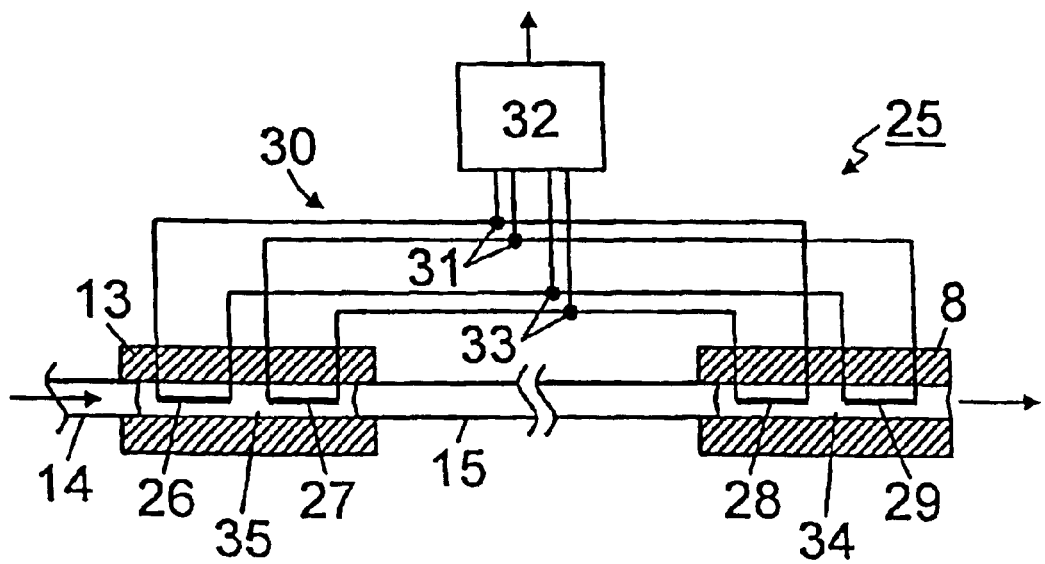

FIG. 3 shows a thermal conductivity detector 25, which alternately works as the detector device 8 and the additional detector device 13. The heat conductivity detector 25 has four wire type heating resistors 26, 27, 28 and 29 which are arranged in a bridge circuit 30. The bridge circuit 30 is supplied with a current from a detector circuit 32 at two circuit points 31 located opposite each other, and the voltage occurring between the two other circuit points 33 that are located opposite each other is detected by the detector circuit 32 to generate the detector signals 9. The heating resistors 28 and 29 lying diagonally opposite each other in the bridge circuit 30 are arranged at the end of the separation column section 15 in a measuring path 34 of the detector device 8.

The other two heating resistors 26 and 27 are disposed in an additional measuring path 35 of the additional detector device 13 inserted between the two separation column sections 14 and 15. The measuring paths 34 and 35, but especially the measuring path 35, are configured in such a way that their cross-sectional inside dimensions correspond to those of the separation column sections 14 and 15, so that the separation efficiency of the separation device 6 is not affected by the insertion of the additional detector device 13. A dosing plug, which is introduced into the separation device 6 using a carrier gas coming from the processing and dosing unit 5 (FIG. 1), first reaches the measuring path 35 of the additional detector device 13 while the carrier gas flows through the measuring path 34 of the detector device 8. The thermal conductivity detector 25 then works as the additional detector device 13, and the measuring path 34 of the detector device 8 serves as a reference path. When the dosing plug finally reaches the measuring path 34 of the detector device 8, the thermal conductivity detector 25 works as the detector device 8, and the measuring path 35 of the additional detector device 13 through which the carrier gas flows acts as the reference path for the detector device 8. The heating resistors 26, 27, 28 and 29 and the inner walls of the measuring path 34 and 35 are made of materials that are inert with respect to the substance mixture to be analyzed and the carrier gas—.g., gold or silica (quartz)—to exclude any change in the substance mixture as a result of chemical reactions.

The above description of the preferred embodiments has been given by way of example. From the disclosure given, those skilled in the art will not only understand the present invention and its attendant advantages, but will also find apparent various changes and modifications to the structures and methods disclosed. It is sought, therefore, to cover all such changes and modifications as fall within the spirit and scope of the invention, as defined by the appended claims, and equivalents thereof.

What is claimed is:

1. Gas chromatograph comprising:
   a separation device, which separates the substances of a substance mixture supplied to the separation device in a dosed manner and flowing through a path of the separation device,
   a detector device disposed downstream of the separation device, which generates detector signals as a function of the arriving separated substances,
   an evaluation device, connected to the detector device, which, in accordance with the detector signals, provides a quantitative determination of specified substances, based on the detector signals, as a first result,
   an additional detector device, arranged in the path of the separation device, which generates additional detector signals in accordance with the substances that at this stage have not been completely separated,
   a computational unit, connected to the additional detector device, which provides a further quantitative determination of at least a portion of the specified substances, based on the additional detector signals, as an additional result, and
   a process control device controlled by the evaluation device, wherein
   if a rate of change in the additional result of the computational unit is larger than a rate of change in the first result, the process control device uses the additional result at least predominantly, and otherwise the process control device uses the first result of the evaluation device for the process control.

2. Gas chromatograph as claimed in claim 1, wherein the process control device is at least one of an open-loop control device and a closed-loop control device.

3. Gas chromatograph comprising:
   a separation device, which separates the substances of a substance mixture supplied to the separation device in a dosed manner and flowing through a path of the separation device,
   a detector device disposed downstream of the separation device, which generates detector signals as a function of the arriving separated substances,
   an evaluation device, connected to the detector device, which, in accordance with the detector signals, provides a quantitative determination of specified substances, based on the detector signals, as a first result,
   an additional detector device, arranged in the path of the separation device, which generates additional detector signals in accordance with the substances that at this stage have not been completely separated, and
   a computational unit, connected to the additional detector device, which provides a further quantitative determination of at least a portion of the specified substances, based on the additional detector signals, as an additional result
   wherein the computational unit includes:
   a computational algorithm with variable parameters for quantitative determination of the specified substances or the portion thereof,
   a memory unit, which stores the additional result provided by the computational unit,
   a comparator unit, which compares the first result of the evaluation device and the stored additional result of the computational unit, and
   a correction algorithm, which changes the parameters of the computational algorithm as a function of a variance between the result of the evaluation device and the stored additional result of the computational unit in order to reduce the variance.

4. Gas chromatograph as claimed in claim 1, wherein the additional detector device comprises a measuring path, through which the substance mixture flows, having cross-sectional dimensions corresponding substantially the cross-sectional dimensions of the separation device.

5. Gas chromatograph as claimed in claim 4, wherein the additional detector device comprises a thermal conductivity detector with heating resistors arranged in a bridge circuit, and wherein two of the heating resistors, located opposite each other in the two different halves of the bridge, are arranged in the measuring path.

6. Gas chromatograph as claimed in claim 5, wherein the thermal conductivity detector works alternately as the detector device and the additional detector device, and wherein two others of the heating resistors are arranged in a measuring path, through which the substance mixture flows, of the detector device disposed downstream of the separation device.

7. Gas chromatograph as claimed in claim 3, wherein the additional detector device comprises a measuring path, through which the substance mixture flows, having cross-sectional dimensions corresponding substantially the cross-sectional dimensions of the separation device.

8. Gas chromatograph as claimed in claim 7, wherein the additional detector device comprises a thermal conductivity detector with heating resistors arranged in a bridge circuit, and wherein two of the heating resistors, located opposite each other in the two different halves of the bridge, are arranged in the measuring path.

9. Gas chromatograph as claimed in claim 8, wherein the thermal conductivity detector works alternately as the detector device and the additional detector device, and wherein two others of the heating resistors are arranged in a measuring path, through which the substance mixture flows, of the detector device disposed downstream of the separation device.

* * * * *